US012630499B2

(12) United States Patent
Rembiak

(10) Patent No.: US 12,630,499 B2
(45) Date of Patent: May 19, 2026

(54) BENZALDEHYDE OXIMES AND METHOD FOR PRODUCING SAME

(71) Applicant: Bayer Aktiengesellschaft, Leverkusen (DE)

(72) Inventor: Andreas Rembiak, Bad Soden (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 533 days.

(21) Appl. No.: 18/245,683

(22) PCT Filed: Sep. 29, 2021

(86) PCT No.: PCT/EP2021/076812

§ 371 (c)(1),
(2) Date: Mar. 16, 2023

(87) PCT Pub. No.: WO2022/069553

PCT Pub. Date: Apr. 7, 2022

(65) Prior Publication Data

US 2023/0348366 A1 Nov. 2, 2023

(30) Foreign Application Priority Data

Oct. 1, 2020 (EP) .................................... 20199639

(51) Int. Cl.
*C07C 249/08* (2006.01)
*C07C 45/45* (2006.01)

(52) U.S. Cl.
CPC .......... *C07C 249/08* (2013.01); *C07C 45/455* (2013.01)

(58) Field of Classification Search
None
See application file for complete search history.

(56) References Cited

U.S. PATENT DOCUMENTS

| | | | |
|---|---|---|---|
| 4,424,229 | A | 1/1984 | Jorgensen et al. |
| 6,287,646 | B1 | 9/2001 | Takeuchi et al. |
| 9,078,442 | B2 | 7/2015 | Willms et al. |
| 9,516,880 | B2 | 12/2016 | Haaf et al. |
| 9,585,392 | B2 | 3/2017 | Kuhn et al. |
| 10,104,892 | B2 | 10/2018 | Frenzel et al. |
| 11,597,724 | B2 | 3/2023 | Peters et al. |
| 11,613,522 | B2 | 3/2023 | Peters et al. |
| 12,171,230 | B2 | 12/2024 | Trabold et al. |
| 12,185,723 | B2 | 1/2025 | Van Almsick et al. |
| 12,319,664 | B2 | 6/2025 | Bojack et al. |
| 2004/0110990 | A1 | 6/2004 | Eckert et al. |
| 2009/0062342 | A1 | 3/2009 | Bezencon et al. |
| 2022/0053762 | A1 | 2/2022 | Trabold et al. |
| 2022/0306591 | A1 | 9/2022 | Bojack et al. |
| 2022/0386605 | A1 | 12/2022 | Lorentz et al. |
| 2023/0104990 | A1 | 4/2023 | Olenik et al. |
| 2023/0189808 | A1 | 6/2023 | Dittgen et al. |
| 2023/0200390 | A1 | 6/2023 | Dittgen et al. |
| 2023/0200393 | A1 | 6/2023 | Dittgen et al. |
| 2023/0200394 | A1 | 6/2023 | Dittgen et al. |
| 2023/0217926 | A1 | 7/2023 | Dittgen et al. |
| 2023/0240297 | A1 | 8/2023 | Dittgen et al. |
| 2023/0265062 | A1 | 8/2023 | Hoemberger et al. |
| 2023/0276792 | A1 | 9/2023 | Dittgen et al. |
| 2023/0339876 | A1 | 10/2023 | Pazenok et al. |

FOREIGN PATENT DOCUMENTS

| | | | |
|---|---|---|---|
| CN | 101565344 | A | 10/2009 |
| EP | 1389608 | A1 | 2/2004 |
| EP | 1582523 | A1 | 10/2005 |
| JP | 2016166153 | A | 9/2016 |
| WO | 2012130798 | A1 | 10/2012 |
| WO | 2014048827 | A1 | 4/2014 |
| WO | 2014048940 | A2 | 4/2014 |
| WO | 2015039036 | A2 | 3/2015 |
| WO | 2019034602 | A1 | 2/2019 |
| WO | 2019145245 | A1 | 8/2019 |
| WO | 2019224774 | A1 | 11/2019 |
| WO | 2020085446 | A1 | 4/2020 |
| WO | 2022069554 | A1 | 4/2022 |

OTHER PUBLICATIONS

Menzel et al. (Org. Proc. Res. Dev., 2009, 13(3), 519) (Year: 2009).*
Barbachyn, et al., "Identification of Phenylisoxazolines as Novel and Viable Antibacterial Agents Active against Gram-Positive Pathogens", J. Med. Chem. 2003, pp. 284-302, vol. 46.
Bharate, et al., "Montmorillonite clay Cu(II) catalyzed domino one-pot multicomponent synthesis of 3,5-disubstituted isoxazoles", Tetrahedron Letters, 2013, pp. 3558-3561, vol. 54.
Chen, et al., "Synthesis and Mesomorphic Properties of Tolane-Based Fluorinated Liquid Crystals with an Acrylate Linkage", Molecular Crystals and Liquid Crystals, 2010, pp. 138-146, 528-1.
Han, et al., "One-Pot Synthesis of Isoxazolines from Aldehydes Catalyzed by Iodobenzene", Synthesis, 2014, pp. 503-509, vol. 46, New York.

(Continued)

*Primary Examiner* — Renee Claytor
*Assistant Examiner* — Jennifer C Sawyer
(74) *Attorney, Agent, or Firm* — Paul D. Tietz; Michael VanEngelen

(57) ABSTRACT

The present invention relates to a method for preparing benzaldehyde oximes of the general formula (I) and to the use thereof as important precursors for the synthesis of agrochemical and pharmaceutical active substances (I)

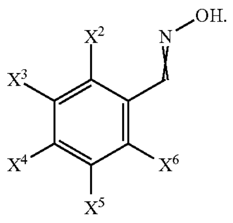

14 Claims, No Drawings

(56) References Cited

OTHER PUBLICATIONS

International Preliminary Report on Patentability from PCT Application No. PCT/EP2021/076812, mailed Mar. 28, 2023.
Stotani, et al., "A Versatile Strategy for the Synthesis of 4,5-Dihydroxy-2,3-Pentanedione (DPD) and Related Compounds as Potential Modulators of Bacterial Quorum Sensing", Molecules, 2018, pp. 2545, 23.
Troshin, et al., "Electrophilicities of Symmetrically Substituted 1,3-Diarylallyl Cations", The Journal of Organic Chemistry, 2011, pp. 9391-9408, vol. 76.
Yang, et al., "Highly Efficient and Catalytic Conversion of Aldoximes to Nitriles", Organic Letters, 2001, pp. 4209-4211, vol. 3, No. 26.
Gopalsamy, et al., "Design of Potent mRNA Decapping Scavenger Enzyme (DcpS) Inhibitors with Improved Physicochemical Properties to Investigate the Mechanism of Therapeutic Benefit in Spinal Muscular Atrophy (SMA)", Journal of Medicinal, 2017, pp. 3094-3108, 60.

* cited by examiner

BENZALDEHYDE OXIMES AND METHOD FOR PRODUCING SAME

The present application is a 35 U.S.C. § 371 national phase entry of International Application No. PCT/EP2021/076812, filed on Sep. 29, 2021, which claims priority to European Patent Application No. 20199639.4, filed Oct. 1, 2020, the contents of each of which are hereby incorporated by reference in their entirety.

Benzaldehyde oximes are an important precursor of agrochemical (e.g. WO 2014/048827A1 or WO 2019/145245A1) and pharmaceutical (e.g. *J. Med. Chem.* 2003, 46, 284) phenylisoxazoline-containing active substances.

The preparation of benzaldehyde oximes starting from the corresponding benzaldehydes is described numerous times in the literature, for example in Org. Lett. 2001, 3, 4209 (reaction in organic solvent with addition of base), JP2016166153A (two-phase system), US 20090062342A1 (aqueous system with addition of a phase-transfer catalyst and an inorganic base) or in Molecules 2018, 23, 2545 (aqueous system with addition of an organic base). WO 2012/130798 A1 and WO 2014/048827 A1 describe the preparation of the oxime from 3,5-difluorobenzaldehyde.

The preparation of 3,5-difluorobenzaldehyde is described e.g. in U.S. Pat. Nos. 4,424,229A, 6,287,646B1 and also in Mol. Crystals and Liquid Crystals 2010, 528, 138 with the use of magnesium by means of Grignard formation. As an alternative, the use of turbo Grignard has previously been described in EP 1582523A1 and the use of sec-butyllithium in J. Org. Chem. 2011, 76, 9391. In addition, EP 1389608A1 described its preparation by metal-catalysed cyanation and subsequent reduction, and WO 2019/224774A1 and CN 101565344A the oxidation of the corresponding benzyl alcohol.

There is an abundance of literature for the preparation of benzaldehyde oximes in two steps starting from halogenated benzene via the benzaldehyde to the corresponding oxime. However, no method has yet been described in which these two reaction steps are carried out without isolation of the intermediate product. The isolation of the aldehyde is a critical step on account of its volatility and its sensitivity to oxidation by atmospheric oxygen and leads to the formation of unwanted by-products and to a reduction in yield. It would therefore be desirable to circumvent the isolation.

In the light of the prior art described above, the object of the present invention is to find a method for preparing the compounds of the general formula (I) with which they may be obtained in higher yield, in high purity and in an environmentally friendly manner, in order that important intermediates for the preparation of active substances may be obtained on an industrial scale.

The object described above is achieved by a method for preparing compounds of the general formula (I)

(I)

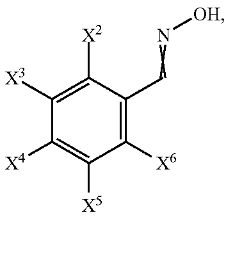

in which $X^2$ is H, $C_1$-$C_4$ alkyl, $C_1$-$C_4$ fluoroalkyl, $C_1$-$C_4$ fluoroxyalkyl, $C_1$-$C_4$ alkoxy, fluorine, CN, $X^3$ is H, $C_1$-$C_4$ alkyl, $C_1$-$C_4$ fluoroalkyl, $C_1$-$C_4$ fluoroxyalkyl, $C_1$-$C_4$ alkoxy, fluorine, chlorine, CN, $X^4$ is H, $C_1$-$C_4$ alkyl, $C_1$-$C_4$ fluoroalkyl, $C_1$-$C_4$ fluoroxyalkyl, $C_1$-$C_4$ alkoxy, fluorine, CN, $X^5$ is H, $C_1$-$C_4$ alkyl, $C_1$-$C_4$ fluoroalkyl, $C_1$-$C_4$ fluoroxyalkyl, $C_1$-$C_4$ alkoxy, fluorine, chlorine, CN, $X^6$ is H, $C_1$-$C_4$ alkyl, $C_1$-$C_4$ fluoroalkyl, $C_1$-$C_4$ fluoroxyalkyl, $C_1$-$C_4$ alkoxy, fluorine, CN, and wherein the compounds of the general formula (II)

(II)

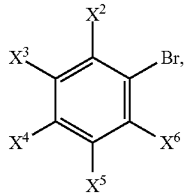

in which the radicals are as defined above, are in a first reaction step reacted in the presence of isopropylmagnesium chloride and DMF to form corresponding adducts (III), which in a second reaction step with addition of acid and hydroxylamine react further to aldehydes of the general formula (IV)

(IV)

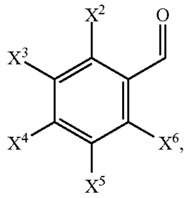

in which the radicals are as defined above, with the subsequent formation of the compounds of the general formula (I).

Preferred definitions of the radicals in the compounds of the general formulas (I), (II), (III) and (IV) are as follows:

$X^2$ is H, methyl, trifluoromethyl, difluoromethyl, difluoromethoxy, trifluoromethoxy, fluorine, methoxy, CN, $X^3$ is H, methyl, trifluoromethyl, difluoromethyl, difluoromethoxy, trifluoromethoxy, fluorine, chlorine, methoxy, CN, $X^4$ is H, methyl, trifluoromethyl, difluoromethyl, difluoromethoxy, trifluoromethoxy, fluorine, methoxy, CN, $X^5$ is H, methyl, trifluoromethyl, difluoromethyl, difluoromethoxy, trifluoromethoxy, fluorine, chlorine, methoxy, CN, $X^6$ is H, methyl, trifluoromethyl, difluoromethyl, difluoromethoxy, trifluoromethoxy, fluorine, methoxy, CN.

Particularly preferred definitions of the radicals in the compounds of the general formulas (I), (II), (III) and (IV) are as follows:

$X^2$ is H, $X^3$ is H, methyl, trifluoromethyl, difluoromethyl, fluorine, chlorine, methoxy, CN, $X^4$ is fluorine, H, $X^5$ is H, methyl, trifluoromethyl, difluoromethyl, fluorine, chlorine, methoxy, CN, $X^6$ is H.

Very particularly preferred definitions of the radicals in the compounds of the general formulas (I), (II), (III) and (IV) are as follows:

$X^2$ is H,
$X^3$ is H, fluorine,
$X^4$ is H, fluorine,
$X^5$ is H, fluorine,
$X^6$ is H.

Most preferred definitions of the radicals in the compounds of the general formulas (I), (II), (III) and (IV) are as follows:

$X^2$ is H,
$X^3$ is fluorine,
$X^4$ is H,
$X^5$ is fluorine,
$X^6$ is H.

DESCRIPTION OF THE METHODS AND INTERMEDIATES ing aldehyde (IV) undergoing a continuous reaction to form compounds of the general formula (I).

The compounds of the formula (I) may be present as mixtures of geometric isomers:

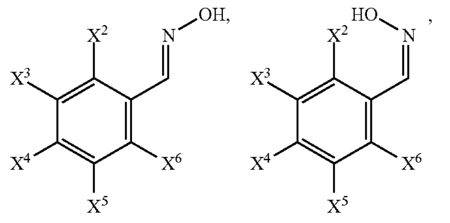

(E)-Isomer (Z)-Isomer

The ratio between the E- and Z-isomers varies, the E-isomer generally being present in greater quantity.

Scheme 1

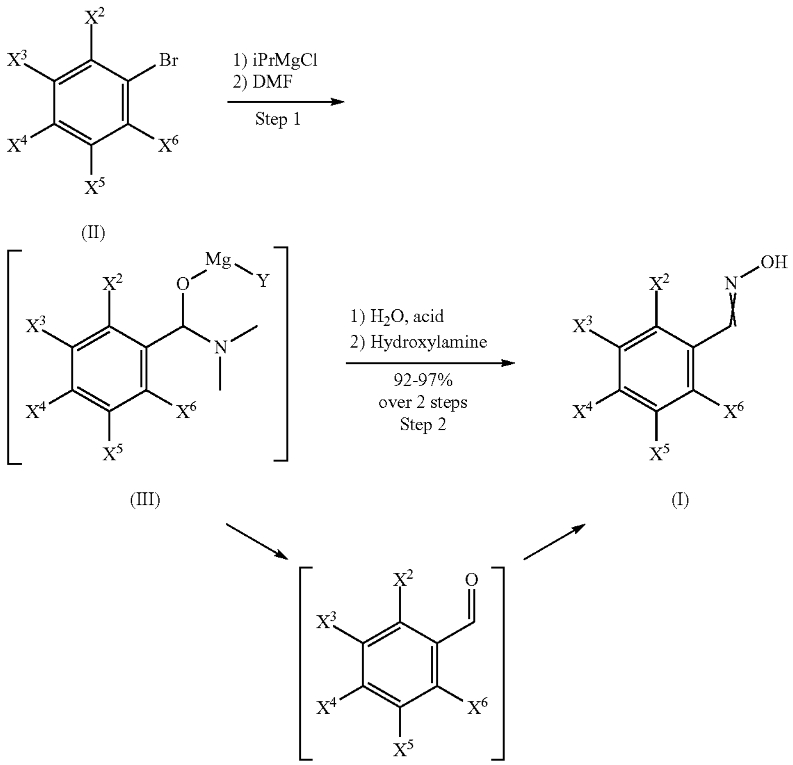

(II)

(III)

(I)

(IV)

To the compounds of the general formula (II) is added in the first step, with constant cooling, isopropylmagnesium chloride, which can be used directly in the form of the commercially available solution, for example as a 2 molar solution in THF, or is preformed from magnesium and 2-propyl chloride in a suitable solvent, for example THF. The reaction mixture is then treated with DMF (N,N-dimethylformamide). The corresponding DMF adduct (III) is obtained, to which is added, without workup and with constant cooling, aqueous acid and hydroxylamine (in the form of the salt or as an aqueous solution), the correspond- Reaction Step 1

The first reaction step is carried out in a suitable solvent.

Suitable solvents are in principle all organic solvents that are inert under the specific reaction conditions, for example aliphatic, cycloaliphatic or aromatic hydrocarbons (e.g. pentane, hexane, heptane, octane, nonane and technical grade hydrocarbons, cyclohexane, methylcyclohexane, petroleum ether, ligroin, benzene, toluene, xylene, mesitylene), aliphatic, cycloaliphatic or aromatic ethers (e.g. 1,2-dimethoxyethane (DME), diglyme, tetrahydrofuran (THF), 2-methyl-THF, 1,4-dioxane, methyl tert-butyl ether (MTBE), cyclopentyl methyl ether, anisole) or mixtures of the stated solvents. Preferably, the first reaction step is carried out in toluene, xylene, mesitylene, anisole, THF, methylcyclohexane, 2-methyl-THF or methyl tert-butyl ether or in a mixture of said solvents. More preferably, toluene, THF or a mixture of toluene and THF is used. More preferably, the solvent is an anhydrous solvent.

In addition, the reaction mixture is cooled during the addition of isopropylmagnesium chloride. Preferably, the reaction is carried out at temperatures of between −10° C. and 20° C., more preferably at temperatures of between 0° C. and 15° C. The addition of DMF preferably takes place at temperatures of between −10° C. and 60° C., more preferably at temperatures of between 0° C. and 30° C. Very particularly preferably, the addition of DMF to the reaction mixture takes place at the same temperature as the addition of isopropylmagnesium chloride. Reaction step 1 is here carried out by metered addition of the compounds of the general formula (II), in the form of the pure substance or as a solution in a suitable solvent, to a solution of isopropylmagnesium chloride.

Preferably, reaction step 1 takes place through metered addition of isopropylmagnesium chloride into a solution of the compounds of the general formula (II). This is followed by metered addition of the reaction mixture to a solution of DMF, more preferably DMF is metered into the reaction mixture.

Isopropylmagnesium chloride is used in equimolar amounts or in excess, preferably 5.0 to 1.05 equivalents, more preferably 2.0 to 1.05 equivalents.

DMF is used in equimolar amounts or in excess, preferably 5.0 to 1.05 equivalents, more preferably 2.0 to 1.05 equivalents.

The isopropylmagnesium chloride can be used in the form of the commercial solution, as a 2 molar solution in THF, or it can be self-prepared in situ. For this, metallic magnesium is initially charged in a suitable organic solvent that is inert under the reaction conditions, particularly preferably diethyl ether or tetrahydrofuran, and 2-chloropropane is added. Activation of the magnesium by methods generally known to those skilled in the art, for example activation by iodine, dibromomethane or by addition of active isopropylmagnesium chloride, can optionally be carried out. This is followed by reaction step 1, preferably by the metered addition of the compounds of the general formula (II) into the solution of isopropylmagnesium chloride described in accordance with the invention.

Reaction Step 2

The second reaction step is carried out in aqueous solution.

In addition, the reaction mixture is cooled during hydrolysis of the reaction mixture/during addition of aqueous acid and hydroxylamine in the form of an aqueous solution of a salt or of the free base. Preferably, the reaction is carried out at temperatures within a range of between 0° C. and 40° C., more preferably at temperatures of between 0° C. and 30° C.

The hydrolysis of the reaction mixture from reaction step 1 can be effected by addition of an aqueous acid or of water, preferably the hydrolysis is effected by metered addition of the reaction mixture to aqueous acid or water, more preferably by metered addition of the reaction mixture to water.

The acid used is preferably aqueous hydrochloric acid or aqueous sulfuric acid, more preferably aqueous sulfuric acid. The sulfuric acid may already be present before the hydrolysis of the reaction mixture, preferably the sulfuric acid is metered in after the hydrolysis of the reaction mixture in water under the preferred conditions has taken place. The aqueous sulfuric acid is preferably used in concentrations of between 1% and 80% by weight, more preferably in concentrations of between 10% and 50% by weight. Preferably, 0.2 to 5.0 equivalents of sulfuric acid are used, more preferably 0.3 to 2 equivalents.

Hydroxylamine is preferably used in the form of the chloride salt ($NH_2OH·HCl$) or sulfate salt ($(NH_2OH)_2·H_2SO_4$), in the form of the pure substance or as an aqueous solution, or as an aqueous solution of the free base ($NH_2OH$), more preferably it is used as an aqueous solution of the sulfate salt. This solution is preferably used in concentrations of between 5% and 40% by weight, more preferably between 15% and 35% by weight. Preferably, 0.5 to 0.7 equivalents of $(NH_2OH)_2·H_2SO_4$ are used, more preferably 0.55 to 0.6 equivalents.

On completion of the reaction, the workup and isolation of the compounds of the general formula (I) can take place e.g. by phase separation, extraction of the aqueous phase with a suitable organic solvent, washing of the organic phase with water, and complete or partial removal of the solvent.

The compounds of the general formula (I) can be isolated in the form of the solid substance or as a solution in a suitable solvent.

The yield is 92 to 97 percent over two steps, compared with 55 to 79 percent over 2 steps by way of comparison with the prior art.

EXAMPLES

The present invention is elucidated in more detail by the examples that follow, without restriction of the invention thereto.

Measurement Methods

The products were characterized by 1H/19F NMR.

Example 1

(1E)-3,5-Difluorobenzaldehyde Oxime (I-1)

A 1 L four-necked flask with mechanical stirrer was charged under an argon atmosphere with 100.0 g (1.0 equiv.) of 1-bromo-3,5-difluorobenzene in 100 ml of toluene and to this was added dropwise at 0-5° C. over a period of 1.5 hours 279.3 ml of commercial isopropylmagnesium chloride (275.3 g, 2 M in THF, 1.1 equiv.) at <10° C. At the end of the addition, the mixture was stirred for a further 3 h at <5° C. and then 40.8 g (1.1 equiv.) of N,N-dimethylformamide was metered in at <10° C. over a period of 60 min. After stirring at this temperature for a further 15-20 min, the reaction mixture was slowly added over a period of 30 min to 500 ml of water that had been precooled to <5° C. The internal temperature during this process was maintained at <10° C. At the end of the addition, 29.9 g (0.3 equiv.) of 50% sulfuric acid was metered in at <10° C. over a period of 30 min. This was followed by the metered addition of a solution of 45.8 g (0.55 equiv.) of hydroxylamine sulfate in 120 ml of water at <5° C. over a period of 45 min and the reaction mixture was at the end of the addition stirred for a further 3 h, during which time the temperature increased to 20-25° C. After adding a further 100 ml of toluene, the phases were separated and the organic phase was washed with 200 ml of water. Partial removal of the solvent of the organic phase at 100-150 mbar and 40° C. afforded the product as a solution in toluene/THF: 240.0 g (31.5% by weight, 95% yield).

$^1H$ NMR (600 MHz, $CDCl_3$): δ 6.83 ppm (m, 1H), 7.09 (m, 2H), 7.64 (br s, 1H), 8.06 (s, 1H) ppm.

$^{19}F$ NMR (600 MHz, $CDCl_3$): δ −109.0 (2F) ppm.

Example 2

(1E)-3,5-Difluorobenzaldehyde Oxime (I-1)

A 500 ml reactor was charged under argon with 6.8 g (1.1 equiv.) of magnesium in 10 ml of THF, which was activated with 2 ml (0.01 equiv., 2 M in THF) of commercial isopropylmagnesium chloride. This was followed by the metered addition in parallel of 21.9 g (1.1 equiv.) of 2-propyl chloride and 65 ml of THF at 30° C. over a period of 1 h. The reaction mixture was stirred at this temperature for one hour further, then cooled to <5° C. and a solution of 50.0 g (1.0 equiv.) of 1-bromo-3,5-difluorobromobenzene in 50 ml of toluene was metered into it at this temperature over a period of 1 h, at the end of which the mixture was stirred at this temperature for a further 3 h, followed by the metered addition of 20.4 g (1.1 equiv.) of N,N-dimethylformamide at <10° C. over a period of 30 min. After stirring at this temperature for a further 15-20 min, the reaction mixture was added over a period of 30 min to 250 ml of water cooled to <5° C. and the internal temperature maintained at <10° C. At the end of the metered addition, 14.9 g (0.3 equiv.) of 50% sulfuric acid was metered in at <10° C. over a period of 30 min. This was followed by the metered addition of a solution of 22.9 g (0.55 equiv.) of hydroxylamine sulfate in 50 ml of water at <5° C. over a period of 45 min and the reaction mixture was at the end of the addition stirred for a further 3 h, during which time the temperature increased to 20-25° C. After adding a further 50 ml of toluene, the phases were separated and the organic phase was washed with 100 ml of water. Partial removal of the solvent of the organic phase at 100-150 mbar and 40° C. afforded the product as a solution in toluene/THF: 150.0 g (24.9% by weight, 94% yield).

The reactions (Examples 1 and 2) can be carried out in an analogous manner in the following solvents too:

| Solvent instead of toluene | Yield |
|---|---|
| MTBE | 99.6 |
| Methylcyclohexane | 92.9 |
| 2-Methyltetrahydrofuran | 73.2 |
| Xylene | 81.4 |
| Anisole | 73.4 |

The following compounds were additionally prepared using the method of the invention:

3,5-Dichlorobenzaldehyde oxime $^1$H NMR (400 MHz, $CDCl_3$): δ 7.37 (t, J=1.9 Hz, 1H), 7.45 (br s, 1H), 7.46 (d, J=7.5 Hz, 2H), 8.03 (s, 1H) ppm.

3-Fluoro-5-Methoxybenzaldehyde Oxime $^1$H NMR (400 MHz, $CDCl_3$): δ 3.79 (s, 3H), 6.85 (dt, J=2.3/11.0 Hz, 1H), 6.97-7.01 (m, 2H), 8.11 (s, 1H) ppm.

3-Fluoro-5-Methylbenzaldehyde Oxime $^1$H NMR (400 MHz, $CDCl_3$): δ 2.37 ppm (s, 3H), 7.09 (m, 2H), 6.89 (d, J=9.4 Hz, 1H), 7.10-7.14 (m, 2H), 7.46 (br s, 1H), 8.07 (s, 1H) ppm.

The invention claimed is:

1. A method for preparing a compound of formula (I)

(I)

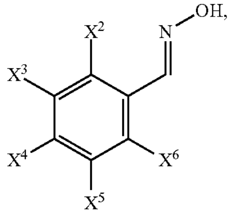

in which formula (I) includes both (E) and (Z) isomers, and wherein $X^2$ is H, $C_1$-$C_4$ alkyl, $C_1$-$C_4$ fluoroalkyl, $C_1$-$C_4$ fluoroxyalkyl, $C_1$-$C_4$ alkoxy, fluorine, or CN;

$X^3$ is H, $C_1$-$C_4$ alkyl, $C_1$-$C_4$ fluoroalkyl, $C_1$-$C_4$ fluoroxyalkyl, $C_1$-$C_4$ alkoxy, fluorine, chlorine, or CN;

$X^4$ is H, $C_1$-$C_4$ alkyl, $C_1$-$C_4$ fluoroalkyl, $C_1$-$C_4$ fluoroxyalkyl, $C_1$-$C_4$ alkoxy, fluorine, or CN;

$X^5$ is H, $C_1$-$C_4$ alkyl, $C_1$-$C_4$ fluoroalkyl, $C_1$-$C_4$ fluoroxyalkyl, $C_1$-$C_4$ alkoxy, fluorine, chlorine, or CN; and $X^6$ is H, $C_1$-$C_4$ alkyl, $C_1$-$C_4$ fluoroalkyl, $C_1$-$C_4$ fluoroxyalkyl, $C_1$-$C_4$ alkoxy, fluorine, or CN;

and wherein the compounds of formula (II)

(II)

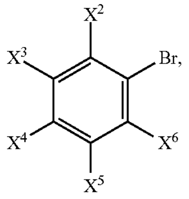

in which the radicals are as defined above, are in a first reaction step reacted in the presence of isopropylmagnesium chloride and dimethylformamide (DMF) to form corresponding adducts of formula (III), (III)

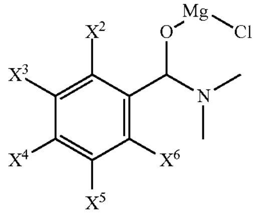

which in a second reaction step with addition of acid and hydroxylamine react further to aldehydes of formula (IV)

(IV)

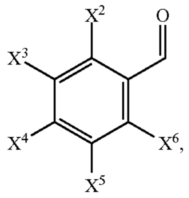

in which the radicals are as defined above, and undergoes continuous reaction to form the compounds of the formula (I).

2. The method according to claim 1, wherein the radicals are defined as follows:

$X^2$ is H, methyl, trifluoromethyl, difluoromethyl, difluoromethoxy, trifluoromethoxy, fluorine, methoxy, or CN;

$X^3$ is H, methyl, trifluoromethyl, difluoromethyl, difluoromethoxy, trifluoromethoxy, fluorine, chlorine, methoxy, or CN;

$X^4$ is H, methyl, trifluoromethyl, difluoromethyl, difluoromethoxy, trifluoromethoxy, fluorine, methoxy, or CN;

$X^5$ is H, methyl, trifluoromethyl, difluoromethyl, difluoromethoxy, trifluoromethoxy, fluorine, chlorine, methoxy, or CN; and $X^6$ is H, methyl, trifluoromethyl, difluoromethyl, difluoromethoxy, trifluoromethoxy, fluorine, methoxy, or CN.

3. The method according to claim 1, wherein the radicals are defined as follows:

$X^2$ is H;

$X^3$ is H, methyl, trifluoromethyl, difluoromethyl, fluorine, chlorine, methoxy, or CN;

$X^4$ is fluorine or H;

$X^5$ is H, methyl, trifluoromethyl, difluoromethyl, fluorine, chlorine, methoxy, or CN; and $X^6$ is H.

4. The method according to claim 1, wherein the radicals are defined as follows:

$X^2$ is H;

$X^3$ is H or fluorine;

$X^4$ is H or fluorine;

$X^5$ is H or fluorine; and $X^6$ is H.

5. The method according to claim 1, wherein the radicals are defined as follows:

$X^2$ is H;

$X^3$ is fluorine;

$X^4$ is H;

$X^5$ is fluorine; and $X^6$ is H.

6. The method according to claim 1, characterized in that the first step of the reaction is carried out in anhydrous solvent.

7. The method according to claim 1, characterized in that the first step of the reaction is carried out in toluene or tetrahydrofuran or in a mixture of these two solvents.

8. The method according to claim 1, characterized in that the first step of the reaction is carried out at temperatures of between 0° C. and 30° C. and the addition of DMF to the reaction mixture in the first step takes place at the same temperature as the addition of isopropylmagnesium chloride.

9. The method according to claim 1, characterized in that 2.0 to 1.05 equivalents of isopropylmagnesium chloride based on the compounds of the general formula (II) are used.

10. The method according to claim 1, characterized in that 2.0 to 1.05 equivalents of DMF based on the compounds of the formula (II) are used.

11. The method according to claim 1, characterized in that, in the second step of the reaction, sulfuric acid is used as acid.

12. The method according to claim 1, characterized in that, in the second step of the reaction, the hydroxylamine is used in the form of $(NH_2OH)_2 \cdot H_2SO_4$.

13. The method according to claim 11, characterized in that, in the second step of the reaction, 0.3 to 2 equivalents of sulfuric acid based on the compounds of the formula (II) are used.

14. The method according to claim 12, characterized in that, in the second step of the reaction, 0.5 to 0.7 equivalents of $(NH_2OH)_2 \cdot H_2SO_4$ based on the compounds of the formula (II) are used.

* * * * *